(12) United States Patent
Akisada et al.

(10) Patent No.: US 6,183,426 B1
(45) Date of Patent: Feb. 6, 2001

(54) ULTRASONIC WAVE APPLYING APPARATUS

(75) Inventors: Shosuke Akisada, Shijonawate; Hiromitu Inoue, Kyoto; Hideaki Abe; Kozo Kawai, both of Neyagawa; Motoharu Muto, Osaka; Masayuki Hayashi, Hikone; Shinji Nishimura; Itaru Saida, both of Hikone, all of (JP)

(73) Assignee: Matsushita Electric Works, Ltd., Kadoma (JP)

( * ) Notice: Under 35 U.S.C. 154(b), the term of this patent shall be extended for 0 days.

(21) Appl. No.: 09/147,391
(22) PCT Filed: May 15, 1998
(86) PCT No.: PCT/JP98/02140
§ 371 Date: Dec. 15, 1998
§ 102(e) Date: Dec. 15, 1998
(87) PCT Pub. No.: WO98/51255
PCT Pub. Date: Nov. 19, 1998

(30) Foreign Application Priority Data

May 15, 1997 (JP) .................................................. 9-126073
Sep. 22, 1997 (JP) .................................................. 9-256858

(51) Int. Cl.$^7$ ...................................................... A61H 1/00
(52) U.S. Cl. .............................. 601/2; 310/316; 310/317; 310/320; 310/321; 310/328; 600/437; 600/439; 601/46; 601/80; 604/22
(58) Field of Search ................................ 433/86; 73/620; 601/2, 46, 80; 128/660.03; 320/108; 324/109; 604/22; 310/317, 320, 316, 321, 328

(56) References Cited

U.S. PATENT DOCUMENTS

| | | | |
|---|---|---|---|
| 4,246,792 | * | 1/1981 | Matzuk .................................. 73/620 |
| 4,791,915 | * | 12/1988 | Barsotti et al. .......................... 601/2 |
| 4,820,152 | * | 4/1989 | Warrin et al. ........................... 433/86 |
| 4,866,412 | * | 9/1989 | Rzepczynski .......................... 338/114 |
| 5,435,304 | * | 7/1995 | Oppelt et al. ..................... 128/660.03 |
| 5,460,595 | * | 10/1995 | Hall et al. ............................... 601/2 |
| 5,952,814 | * | 9/1999 | Lerberghe ............................ 320/108 |

FOREIGN PATENT DOCUMENTS

| | | |
|---|---|---|
| 3-63054 | 3/1991 | (JP) . |
| 6-22518 | 3/1994 | (JP) . |
| 9-248213 | 9/1997 | (JP) . |
| WO98/51255 | 11/1998 | (WO) . |

* cited by examiner

Primary Examiner—Marvin M. Lateef
Assistant Examiner—Jeoyuh Lin
(74) Attorney, Agent, or Firm—Arent Fox Kintner Plotkin & Kahn, PLLC

(57) ABSTRACT

An ultrasonic wave applying apparatus which is safe and convenient for use. The apparatus includes an hand-held applicator having a vibration element which is, in use, contact with a skin of a user to apply ultrasonic waves to the skin, a power source providing a DC voltage, an oscillator circuit which is energized by the DC voltage from the power source to generate an oscillating output for driving the vibration element, and a load detecting circuit which monitors whether the vibration element is loaded such as by contact with the skin and provides a load detection signal when the vibration element is so loaded. In addition, a motion detecting circuit is provided to monitor whether the vibration element is moving and give a motion detection signal when the vibration element is so moving. A control circuit is connected to the load detecting circuit and the motion detecting circuit for controlling the driving circuit to reduce the oscillating output being fed to the ultrasonic vibration element when the load detection signal is not received within a predetermined first time period or when the motion detection signal is not continuous over a critical time duration within a predetermined second time period even in the presence of the load detection signal being detected within the first time period.

14 Claims, 12 Drawing Sheets

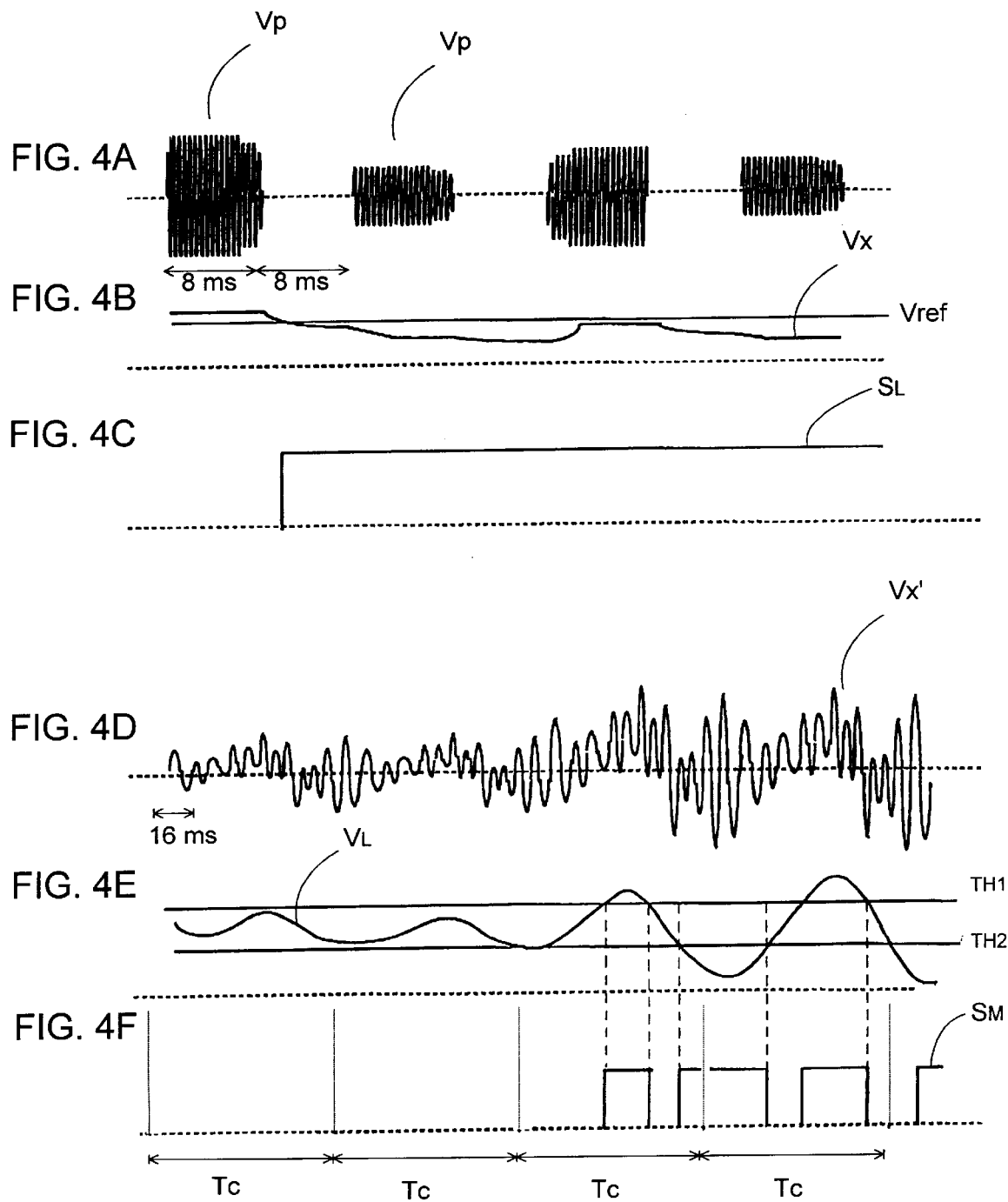

ULTRASONIC WAVE APPLYING APPARATUS

TECHNICAL FIELD

The present invention is directed to an ultrasonic wave applying apparatus for applying ultrasonic waves to a human body.

BACKGROUND ART

Conventional ultrasonic wave applying apparatus for applying ultrasonic waves to the human body are disclosed in Japanese Patent Publication No. 6-22518 and Japanese Patent Laid-Open Publication No. 3-63054. The conventional apparatus includes an applicator having a vibration element which is in contact with the human body to apply the ultrasonic waves, an oscillator circuit for providing ultrasonic waves to the vibration element, and a load detecting circuit which detect whether the vibration element is in contact with a load. In this apparatus, it is proposed to reduce the level of the ultrasonic vibration given to the vibration element upon detection of a no-load condition. The ultrasonic wave applying device of this kind has been developed mainly for diagnosis of internal organs of the human body by a specialist such as a doctor. Therefore, the load detecting circuit is enough by the specialist for effectively applying the ultrasonic waves to the human body. However, when the apparatus is utilized to apply the ultrasonic waves for the purpose of facial care or weight reduction, an user mostly of an amateur is difficult to utilize the apparatus in a safe and effective manner even with the load detecting circuit. Therefore, it becomes important to detect whether the apparatus is correctly moving along the skin. That is, in view of that there may arise a cold burn when the vibration element remains in contact with a portion over a long period, a measure is demanded to prevent the cold burn in addition to eliminating undue energy consumption at the no-load condition.

SUMMARY OF THE INVENTION

The present invention has been accomplished in view of the above and has an object of providing an ultrasonic wave applying apparatus which is safe enough and convenient for use.

The ultrasonic wave applying device in accordance with the present invention includes an hand-held applicator having a vibration element which is, in use, contact with a skin of a user to apply ultrasonic waves to the skin, a power source providing a DC voltage, an oscillator circuit which is energized by the DC voltage from the power source to generate an oscillating output for driving the vibration element, and a load detecting circuit which monitors whether the vibration element is loaded such as by contact with the skin and provides a load detection signal when the vibration element is so loaded. Further, a motion detecting circuit is provided to monitor whether the vibration element is moving and give a motion detection signal when the vibration element is so moving. A control circuit is connected to the load detecting circuit and the motion detecting circuit for controlling the driving circuit to lower the oscillating output being fed to the ultrasonic vibration element when the load detection signal is not received within a predetermined first time period or when the motion detection signal is not continuous over a critical time duration within a predetermined second time period even in the presence of the load detection signal being detected within the first time period.

Thus, the apparatus can detect the motion of the vibration element whether it is moving in contact with the human body and is so made to apply the ultrasonic waves continuously only while the vibration element is so moving, thereby disabling to apply the ultrasonic waves to a portion of the human body over a long period which would otherwise incur cold burn.

Preferably, the apparatus may include a monitoring circuit which gives a single monitoring output indicative of the ultrasonic vibrations being effected by the vibration element and inclusive of a low frequency component which is caused by moving the vibration element and of which frequency is lower than that of the ultrasonic vibrations. The monitoring output is fed to the load detecting circuit as well as to the motion detecting circuit where it is processed to provide the load detection signal and the motion detection signal. The monitoring output including information as to the load condition as well as the motion of the vibration element can appear in a resonant system including the oscillator circuit for the vibration element. Therefore, simple electrical connection of the monitoring circuit to the resonant system can realize the load and motion detection in a simple circuit configuration without requiring an additional sensor for such detection.

For example, the monitoring circuit is arranged to detect an output of the oscillator circuit which includes a transformer with a primary winding and a secondary winding. The vibration element is in the form of a piezoelectric element connected across the secondary winding. The primary winding generates an oscillating voltage which in turn produces the oscillating output across the secondary winding for driving the vibration element. The monitoring circuit includes an auxiliary winding which is magnetically coupled to the transformer for providing the monitoring output in proportion to the output of the oscillator circuit.

Besides, for the same oscillator circuit including the transformer as above, the monitoring circuit may be configured as a rectifier circuit which is connected in parallel with the vibration element across the secondary winding of the transformer to rectify the oscillating voltage into the monitoring output.

Further, the monitoring circuit may be configured to provide the monitoring output based on a current flowing through the oscillator circuit including a resonant circuit. In this case, the oscillator circuit includes the transformer with the primary winding and the secondary winding across which the vibration element in the form of a piezoelectric element is connected. A capacitor is connected across the primary winding to form a parallel resonant circuit with the primary winding. A switching element is connected in series with the parallel resonant circuit across a DC voltage source and is driven to turn on and off for causing the resonant circuit to provide an oscillating voltage which in turn induces the oscillating output across the secondary winding. The monitoring circuit includes a current sensing resistor which is connected in series with the switching element and the parallel resonant circuit to provide the monitoring output in the form of a voltage.

In another version, the monitoring circuit has a transformer with a primary winding and a secondary winding. The primary winding is connected in series with the vibration element in the form of the piezoelectric element in an output path of the oscillator circuit so that the secondary winding provides the monitoring output.

The load detecting circuit is preferred to have a comparator which compares an amplitude of the monitoring output with a predetermined level to provide the load detection signal when the amplitude deviates from the predetermined level by a certain extent.

The motion detecting circuit is arranged to have a low-pass filter to derive the low frequency component from the monitoring output and a judging circuit which provides the motion detection signal to the control circuit when an amplitude of the low frequency component exceeds a predetermined level.

Further, the present invention discloses another arrangement which utilizes a sensor disk disposed adjacent the vibration element for making the load detection and the motion detection. The sensor disk is capable of deforming as a consequence of the vibration element being loaded and is made of pressure sensitive electroconductive rubber which varies its electrical resistance upon being deformed. The sensor disk is formed on its one surface with a single first electrode and on the opposite surface with a plurality of second electrodes. There are provided a plurality of voltage each of which applies a voltage between the first electrode and each of the second electrodes so as to provide a plurality of monitoring outputs each representing degree of deformation occurring at a portion of the sensor disk adjacent to each of the second electrodes. The control circuit is configured to analyze at least one of the monitoring outputs to give the load detection signal and to analyze all of the monitoring outputs with reference to each other in order to provide the motion detection signal.

It is also preferred to make a control by use of a temperature sensor which senses a temperature of the vibration element. A protector circuit is included in the control circuit to produce a stop signal for disabling the oscillator from generating the oscillating output upon receiving the temperature output indicative of the temperature exceeding a critical level. Thus, the vibration element can be protected from contacting with the human body at a heated condition.

The oscillator circuit is preferred to produce the oscillating output intermittently in such a manner as to leave a rest period between adjacent pulse series of the oscillating output. Within this rest period, the load detecting circuit and the motion detecting circuit transmit the load detection signal and the motion detection signal to said control circuit. Thus, the load and motion detection signals can be free from noises to give improved reliability of the judgement at the control circuit.

It is preferred that the oscillator circuit and the power source are incorporated within the applicator together with a battery which supplies a source voltage to the power source, and that the applicator is physically detachable to a main housing which incorporates an inverter providing an AC voltage for charging the battery. The inverter includes a primary power winding across which the AC voltage developed. The applicator incorporates therein a secondary power winding which is magnetically coupled to the primary power winding to induce a corresponding voltage when the applicator is physically connected to the main housing. The secondary power winding is connected within the hand-held applicator to charge said battery by the voltage induced at the secondary power winding. With this arrangement, the applicator can be easily made to have a water-tight structure and can be well utilized in wet environments.

BRIEF DESCRIPTION OF THE DRAWINGS

FIGS. 4A to 4F are explanatory views illustrating operations of the load detecting circuit and the motion detecting circuit;

BEST MODES FOR CARRYING OUT THE INVENTION

Figure 1:
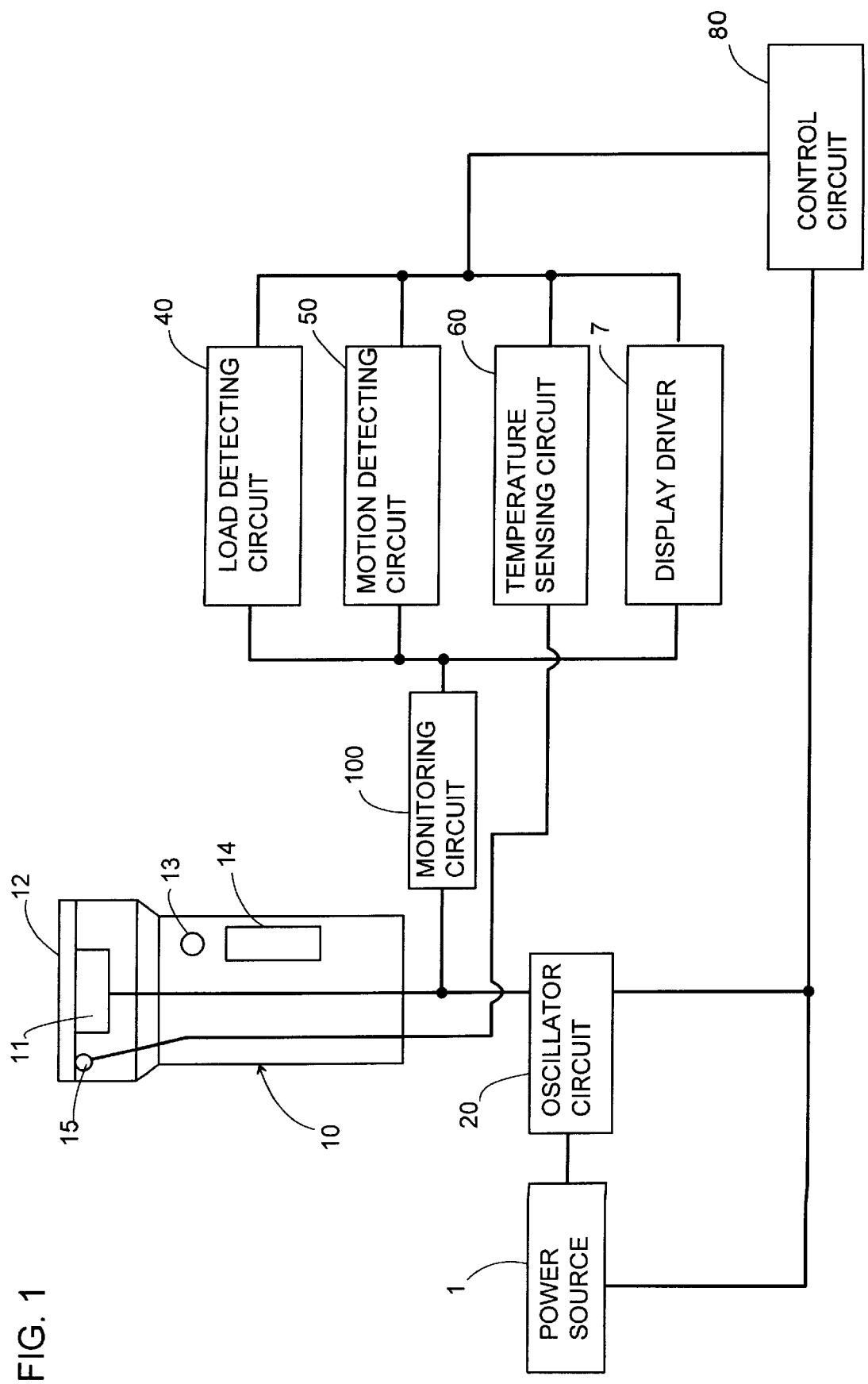
FIG. 1 is a block diagram illustrating a circuit of an ultrasonic wave applying apparatus in accordance with a first embodiment of the present invention.

FIG. 1 illustrates a circuit diagram of an ultrasonic wave applying apparatus in accordance with one embodiment of the present invention. The apparatus is utilized for face cure or weight reduction and includes a hand-held applicator 10 provided at its one end thereof with a vibration plate 12 which is in use to be in contact with a skin of a human body for applying ultrasonic oscillations thereto. The vibration plate 12 is an aluminum-made thin plate and receives an ultrasonic wave produced at an vibration element 11 in the form of a piezoelectric element. In order to make a tight contact with the skin for effectively transmitting the ultrasonic wave, the vibration plate 12 is coated with a gel in use. The gel is made of a substance containing a large amount of water for promoting the transmission of the ultrasonic wave. The applicator 10 includes an oscillator circuit 20 driving the piezoelectric element 11, a power source 1 energizing the oscillator circuit 20, a load detecting circuit 40 for detection a load condition of the vibration plate 12, a motion detecting circuit 50 for detection of a motion of the applicator 10, a temperature sensing circuit 60 for sensing a temperature of the piezoelectric element 11, a display driver 7 for display of operating condition, and a control circuit 80 for control of the above circuits and the like. In addition, the applicator 10 is formed with a power switch 13 and a window 14 for display of the operating condition.

In use, the applicator 10 is required to produce the ultrasonic vibration with the vibration plate 12 kept in contact with the human body. For this purpose, the load detecting circuit 40 is provided to detect whether a suitable load is applied as a consequence of the vibration plate 12 being in contact with the skin of the human body. When the vibration plate 12 is not in tight contact with the skin so as not to transmit the ultrasonic vibration successfully due to no or insufficient coating of the gel, the load detection circuit 40 determines that the vibration plate is not loaded and restricts the generation of the ultrasonic wave. Further, it is desirable to move the vibration plate 12 slowly across the skin when applying the ultrasonic wave to the human body. Otherwise, i.e., when the vibration plate 12 stays at a portion over a long period, there is a potential hazard of causing a cold burn the skin of the human body. In view of this, the motion detecting circuit 50 is provided to enable the continuous oscillation when the vibration plate 12 is moving at a suitable rate and otherwise disable the oscillation. In addition, the control circuit 80 includes a timer which stops the oscillation after the applicator is utilized in a normal condition over a preset time. That is, as will be discussed later, the timer will count a time only when the load detection signal from the load detecting circuit indicates that the vibration plate 12 is kept in contact with the skin and when the motion detection signal from the motion detecting circuit indicates that the vibration plate 12 does not stay at a portion over a long time, the timer operates counting to continue the ultrasonic vibration over the preset time. When the vibration plate 12 makes abnormal vibration with an attendant temperature rise due to malfunction of the oscillator circuit 20 or the like, the temperature sensing circuit 60 is responsive to an output from a temperature sensor 15 located adjacent the vibration plate 12 for providing an output indicative of abnormal temperature rise to the control circuit 80 which in turn responds to stop the oscillator circuit 20.

The window 14 includes an array of light emitting diodes which are driven to turn on and off sequentially for representing the oscillation. In addition, the window 14 displays the normal operation being made, warning of no-load condition, warning of the vibration plate being stationary, warning of abnormal temperature of the vibration plate, remaining time counted by the timer, and erroneous function of the apparatus.

Figure 2:
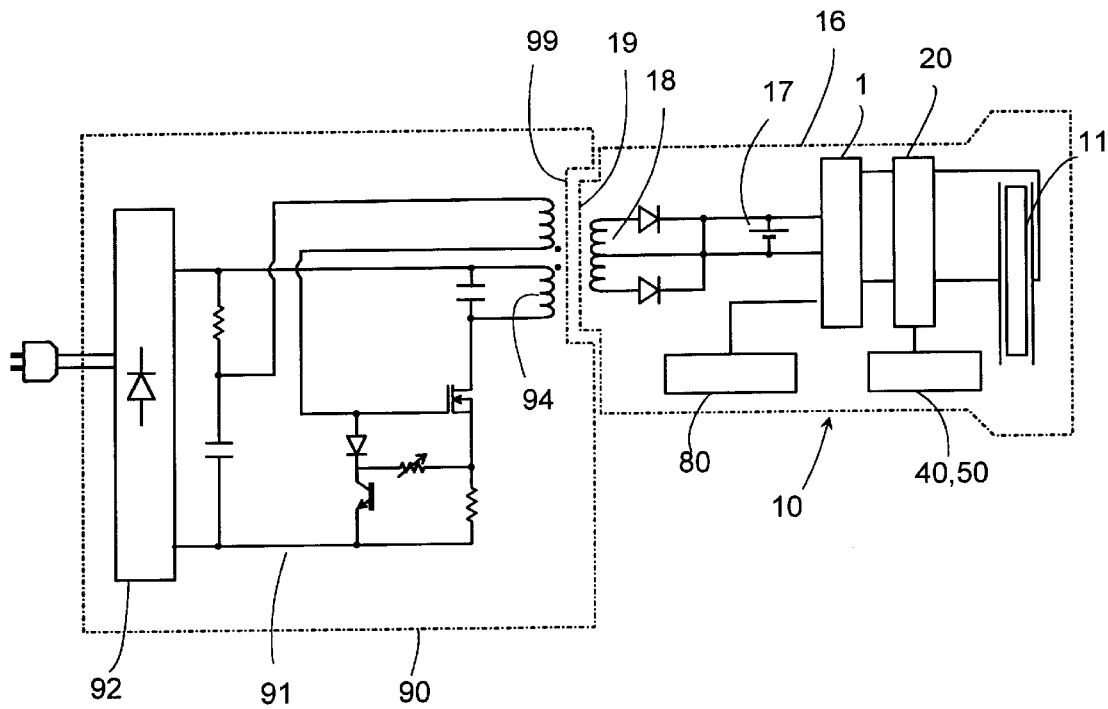
FIG. 2 is a schematic circuit diagram of the apparatus.

As shown in FIG. 2, a housing 16 of the applicator 10 accommodates a rechargeable battery 17 supplying an electric power to the power source 1. The battery 17 is charged by an output from a charger circuit 91 mounted in a separate main housing 90. The charger circuit 91 includes a rectifier 92 for rectification of an AC voltage from a commercial electric source, and an inverter which converts the DC output of the rectifier 92 into an AC output. The inverter includes a primary power winding 94. A corresponding secondary power winding 18 is accommodated within the housing 16 of the applicator 10 so as to be magnetically coupled to the primary power winding 94 when a projection 19 at one end of the housing 16 fits into a recess 99 in the main housing 90, thereby inducing across the secondary power winding 18 a voltage which is proportional to the output voltage of the inverter and is responsible for charging the battery 17. The applicator 10 is detachably mounted to the main housing 90 and receives the electric power therefrom without relying upon electrical contacts. In this respect, the housing 16 is made to be of a water-tight structure so that the applicator can be operated in a wet environment such as in a bathroom or washroom. Thus, the applicator can be free from water invasion trouble when utilized in the bathroom or washroom and can make the use of water available there for the vibration plate 12 instead of the gel.

The power source 1 provides high and low DC voltages from the battery 17 selectively to oscillator circuit for varying magnitude of the oscillating output from the oscillator circuit 20 in accordance with the strength selected by the user. Also, after the preset time of the timer is elapsed, the control circuit 80 gives an instruction to stop providing the electric power to the oscillator circuit 20. FIG. 2 includes motion detecting circuit 50 and load detecting circuit 40.

Figure 3:
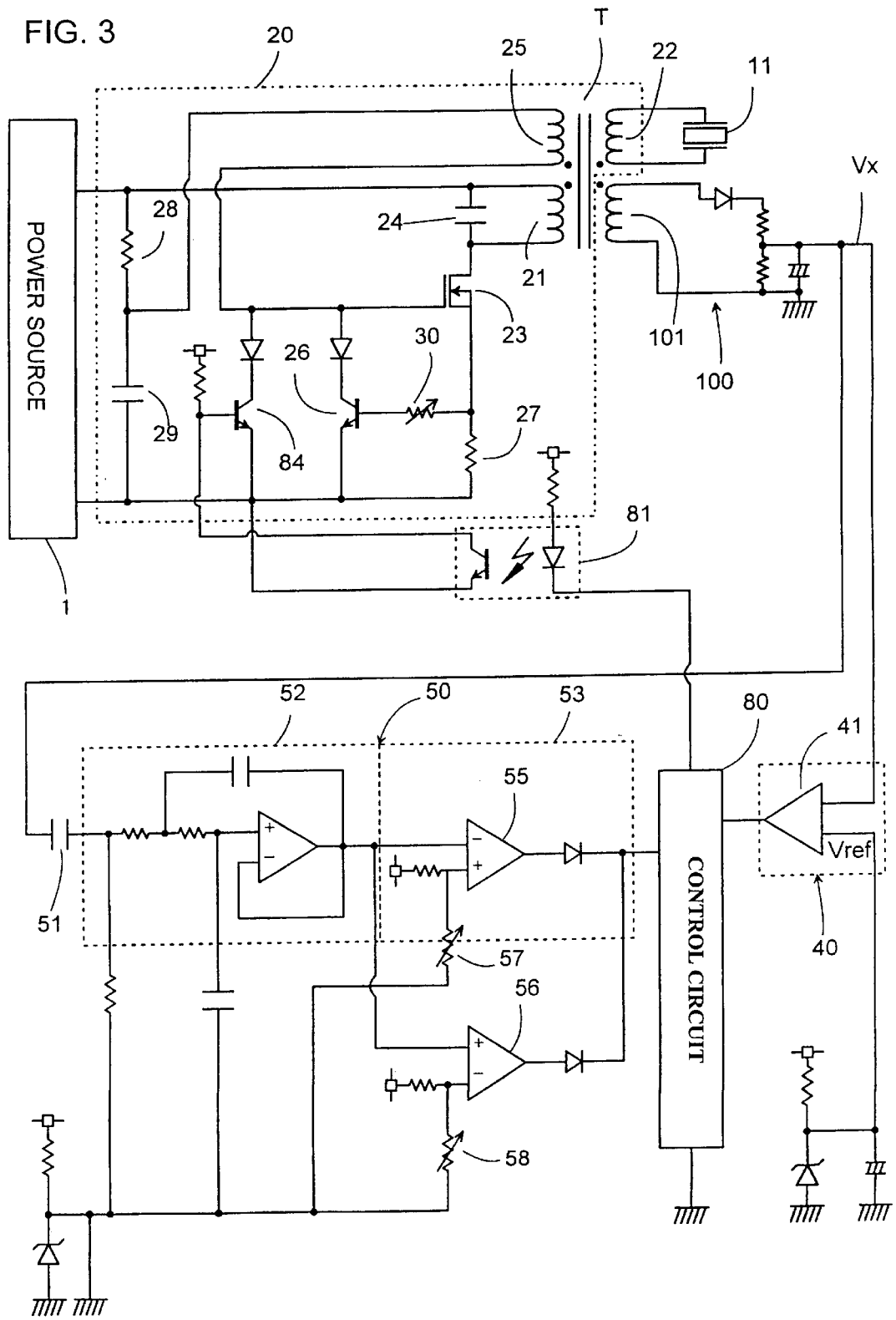
FIG. 3 is a circuit diagram illustrating an oscillator circuit, load detecting circuit, and a motion detecting circuit employed in the above apparatus.

As shown in FIG. 3, the oscillator circuit 20 includes an inverter which converts DC voltage from the power source 1 into an AC voltage having a frequency of about 1 MHz, and which is provided at its output end with a transformer T having a primary winding 21 and a secondary winding 22. The primary winding 21 is connected in series with an FET 23 and a current sensing resistor 27 across the power source 1, and is cooperative with a capacitor 24 connected across the primary winding 21 to form a parallel resonant circuit which provides a resonant voltage across the primary winding 21 upon turning off of FET 23. The piezoelectric element 11 is connected across the secondary winding 22 so as to effect the ultrasonic vibration by the AC voltage induced at the secondary winding 22. A feedback winding 25 is coupled to the primary winding 21 to feedback the output of the oscillator circuit to FET 23. A bipolar transistor 26 is connected in a gate-emitter path of FET 23 for control of FET 23. Connected across the power source 1 is a series combination of a starting resistor 28 and a capacitor 29 of which connection is connected through the feedback winding 25 to a gate of FET 23 to give a bias thereto. When capacitor 29 is charged by the power source to develop a voltage reaching a threshold of FET 23, FET becomes conductive to lower the drain voltage of FET 23. At this time, the feedback winding 25 generates a feedback voltage applied to the gate of FET 23, thereby increasing the current flowing through the FET. Subsequently when a voltage developed across current sensing resistor 27 reaches a predetermined level in correspondence to the increasing current through FET, transistor 26 becomes conductive to turn off FET 23. Thereby, the resonant circuit of primary winding 21 and capacitor 24 becomes active to make a resonance. At the end of one cycle of resonance, the feedback voltage induced at feedback winding 25 reaches a voltage of turning on the gate of FET 23, thereby again making the FET conductive. The above operations are repeated to maintain the resonant voltage so as to oscillate the piezoelectric element 11. The frequency of the resonant circuit is set to be around a natural frequency of piezoelectric element 11 to transmit the resulting ultrasonic vibration to the vibration plate 12.

Connected between the base of transistor 26 and resistor 27 is a variable resistor 30 of which value is varied in order to vary a timing of turning on transistor 26 for adjustment of the resonant frequency. That is, varying the on-time period of FET can adjust the resonant frequency so as to match the resonant frequency of the resonant circuit with the natural frequency of piezoelectric element which may differ due to possible characteristic variation of the element available. It is noted in this connection that the resonant circuit is controlled by the control circuit 80 to give an intermittent oscillation having a rest period between adjacent pulse series Vp, as shown in FIGS. 4A and 4B.

Transformer T includes an auxiliary winding 101 which is cooperative with a rectifier circuit of rectifying the output of auxiliary winding 101 to form a monitoring circuit 100 which gives a monitoring output indicative of a condition of the ultrasonic wave being applied to the load. The monitoring output Vx includes low frequency components which are caused as a result of moving the vibration element 12 and of which frequency is lower than that of the ultrasonic vibration. More precisely, the voltage appearing across auxiliary winding 101 includes low frequency components originating from impedance variation in the piezoelectric element upon contact with the load and from rubbing sounds appearing in response to the applicator moving across the skin of the human body, in addition to high frequency components indicative of the ultrasonic vibration. The monitoring output Vx obtained by rectification of voltage appearing across auxiliary winding 101 is fed to the load detection circuit 40 and the motion detecting circuit 50 for making the load detection and the motion detection.

As shown in FIG. 3, the load detection circuit 40 has a comparator 41 which compares the monitoring output Vx from the monitoring circuit 100 with a reference level Vref. The monitoring output Vx has a waveform pattern as shown in FIG. 4B. When monitoring output Vx becomes lower than the reference level Vref, the comparator 41 provides a H-level load detection signal SL to the control circuit 80 as indicative of that the vibration plate 12 is kept in suitable contact with the skin of the user. When the load detection signal SL is not acknowledged continuously over a predetermined time period, the control circuit 80 stops operating the oscillator circuit 20 or disables the power source 1. In this embodiment, the load detection signal SL is generated when the monitoring output Vx is lower than the reference level Vref in consideration of that the resonant voltage is lowered by the presence of the load. However, in contrast to the above, it is possible that resonant circuit of different configuration may vary the characteristic of the piezoelectric element 11 to break the impedance matching with the resonant circuit, thereby causing the monitoring output to increase in the presence of the load. In this case, it is made to provide the load detection signal SL when the monitoring output Vx exceeds the reference level Vref.

The monitoring output Vx is also fed through a capacitor 51 to the motion detecting circuit 50 in the form of an output Vx', as shown in FIG. 4D. The motion detecting circuit 50 includes a low-pass filter 52 and a judging circuit 53. The output Vx' is removed of high frequency component through the filter 52 to give a low frequency output VL free from the components not caused by the motion of the vibration plate 12, as shown in FIG. 4E. Thus obtained low frequency output VL is fed to two comparators 55 and 56 of the judging circuit 53 and compared respectively with individual thresholds TH1 and TH2 (TH1>TH2) to provide to the control circuit 80 a H-level motion detection signal SM (shown in FIG. 4F) over a period in which the output VL is higher than the threshold TH1 or lower than the threshold TH2. TH1 and TH2 can be adjusted by variable resistors 57 and 58. The control circuit 80 counts the time period of the H-level motion detection signal SM within a predetermined duration Tc (for example, 15 seconds) and determines that the vibration plate 12 has moved suitably when the sum of the counted times within the duration Tc exceeds a predetermined reference. Otherwise, the control circuit 80 determines that no suitable motion has been made and provides a limit signal of limiting the oscillator circuit 20. The oscillator circuit 20 includes a transistor 84 which is connected in parallel with transistor 26 across gate-source path of FET 23 and which is connected to the control circuit 80 through a photo-coupler 81. Thus, upon receiving the limit signal from the control circuit 80, the transistor 84 is turned on to thereby turn off FET 23 for disabling the oscillator circuit 20. Although the limit signal acts to stop the oscillator circuit 20 in this embodiment, the present invention is not limited to this feature and may be arranged to control the oscillator circuit 20 or power supply 1 to reduce the oscillation.

Figures 5A, 5B, 5C:
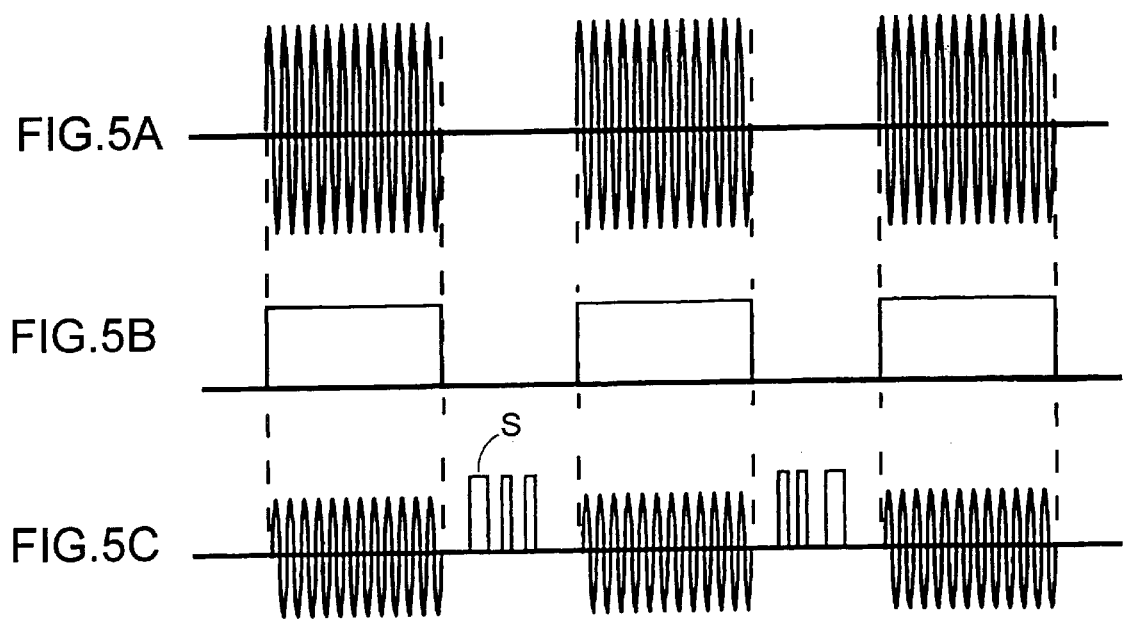
FIGS. 5A to 5C are explanatory views illustrating a relation between an output of the oscillator circuit and an output of the load detecting circuit and the motion detecting circuit.

As shown in FIG. 5A, the output from the oscillator circuit is issued intermittently by use of driving pulses of FIG. 5B. It is within the rest period of the driving pulses that the data signal S including the load detection signal and the motion detection signal is transmitted to be processed at the control circuit 80. Thus, the detection signals can be free from noises associated with the oscillation, thereby realizing reliable load and motion detection.

Figure 6:
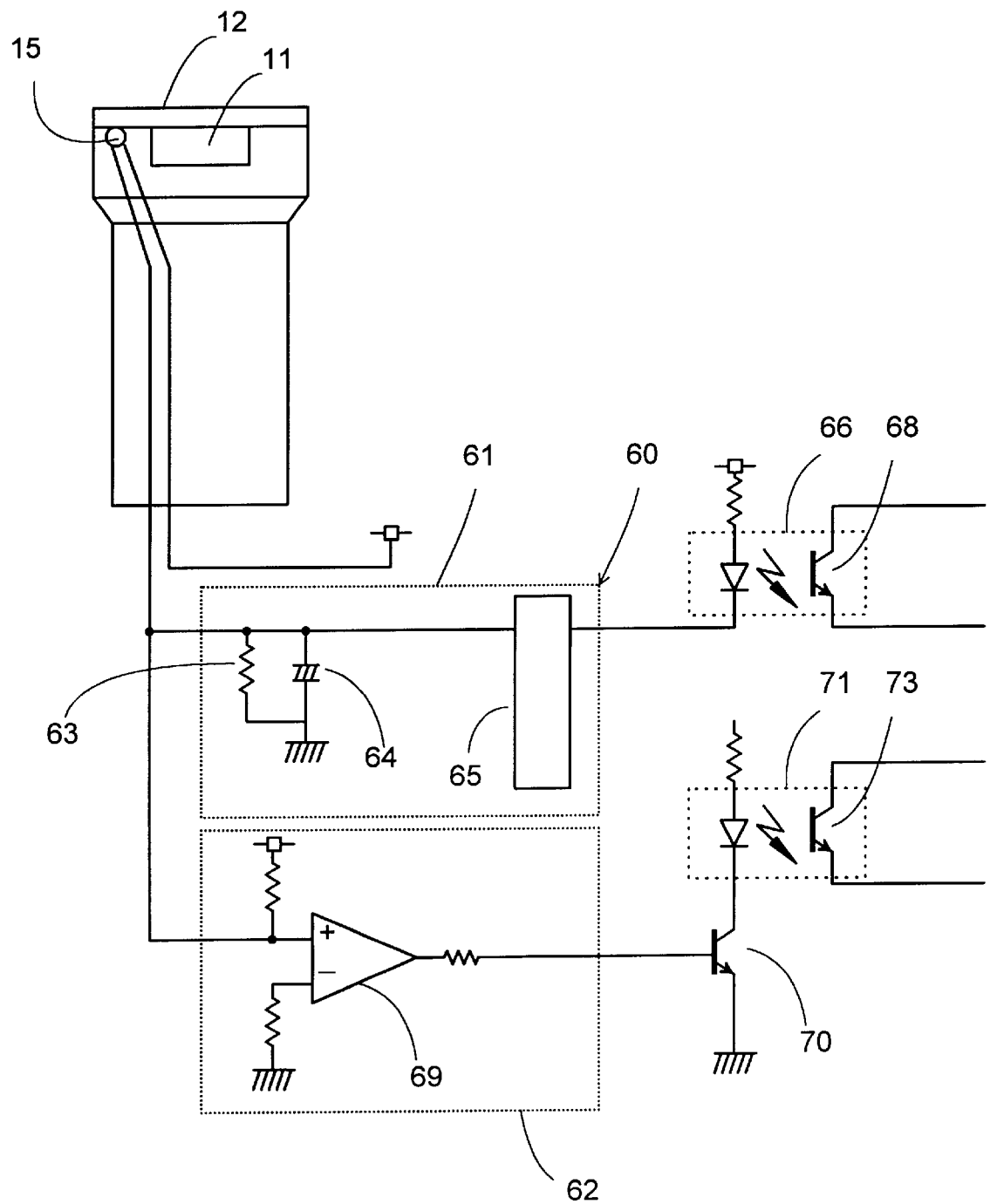
FIG. 6 is a circuit diagram of a temperature sensing circuit employed in the above apparatus.

As shown in FIG. 6, the temperature sensing circuit 60 includes a first temperature sensing section 61 and a second temperature sensing section 62 both receiving an output from a thermistor 15 for temperature sensing. First temperature sensing section 61 has a temperature control 65 to which the output from thermistor 15 is fed through a resistor 63 and a capacitor 64. When the temperature sensed at thermistor 15 is found to exceed a predetermined reference temperature, the temperature control 65 issues a stop signal to the oscillator circuit 20 through a photo-coupler 66. The photo-coupler 66 has a transistor 68 which is connected in a base-emitter path of the transistor 84, so that the stop signal causes the transistor 84 to turn on for stopping the oscillation of the oscillator circuit 20. A hysterics is given to the temperature control such that, after the temperature of the vibration plate 12 sensed by thermistor 15 goes high above the reference temperature, the oscillator circuit 20 is enabled to resume the oscillation only after the sensed temperature goes below a temperature level which is lower than the reference temperature. When the sensed temperature goes below the temperature level, the temperature control 62 responds not to issue the stop signal, thereby resuming the oscillation at the oscillator circuit 20. The second temperature sensing section 62 includes a comparator 69 which operates to turn on a transistor 70 when the temperature sensed at thermistor 15 exceeds a predetermined reference, thereby turning on a transistor 73 of a photo-coupler 71 and consequently disabling the power source 1 connected to transistor 73. The predetermined reference for the comparator 69 is set to be higher than the reference temperature of the temperature control 65 for stopping the ultrasonic oscillation as a safeguard in response to the vibration plate 12 being abnormally heated even if the temperature control 65 made of a microcomputer should fail to operate. FIG. 6 also depicts vibration element 11.

Figure 7:
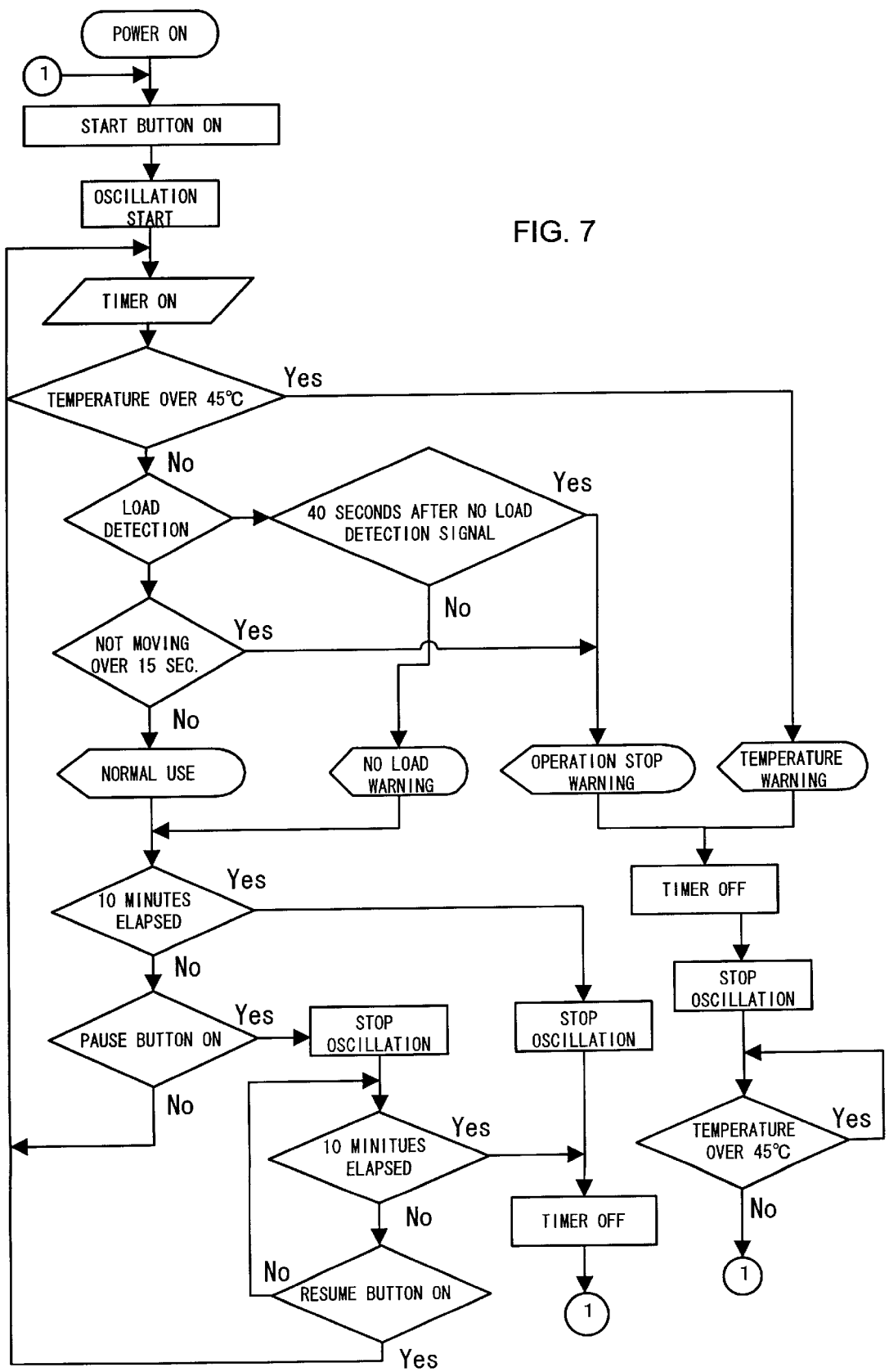
FIG. 7 is a flow chart illustrating operations of the above apparatus.

Operation of the ultrasonic apparatus is now explained with reference to FIG. 7. After turning on a power switch, pressing of a start button actuates the oscillator circuit 20, causing the vibration plate 12 to start the ultrasonic vibration, and starts the timer. At this time, the temperature sensing is made for the vibration plate 12 so that when the first temperature sensing section 61 sees the temperature exceeding, for example, 45°, the display driver 7 gives the temperature warning that the vibration plate is over-heated, and at the same time the timer and the oscillation are stopped. When the sensed temperature is found to be less than 45° at a step after starting the timer, the load detection is made and the motion detection is made subsequently when the load detection signal is issued as indicative of that the vibration plate is loaded. When no load detection signal is issued, a no-load warning is displayed for a limited time period of 40 seconds, for example, urging the user to apply the gel coated vibration plate on the skin. After elapse of 40 seconds with no load detection signal, a control is made to display a warning of stopping the operation and stop the timer and the oscillation. The motion detection is made in the presence of the load detection signal so that, when the motion detection signal is issued within, for example, 15 seconds, a display of normal operation is made and a count-down instruction is given to the timer. After the elapse of a predetermined operation time, say, 10 minutes in this condition, the oscillator circuit is stopped. A pause button is pressed within 10 minutes, the oscillator circuit is stopped but with the timer operating continuously to count down. When a restart button is pressed within this 10 minutes, the oscillator circuit resume the oscillation.

Although the above embodiment is so designed that the control circuit disables the oscillator circuit when no load or no motion is detected, the present invention is not limited to this feature and is designed to reduce the oscillation output from the oscillator circuit upon such detection.

Figure 8:
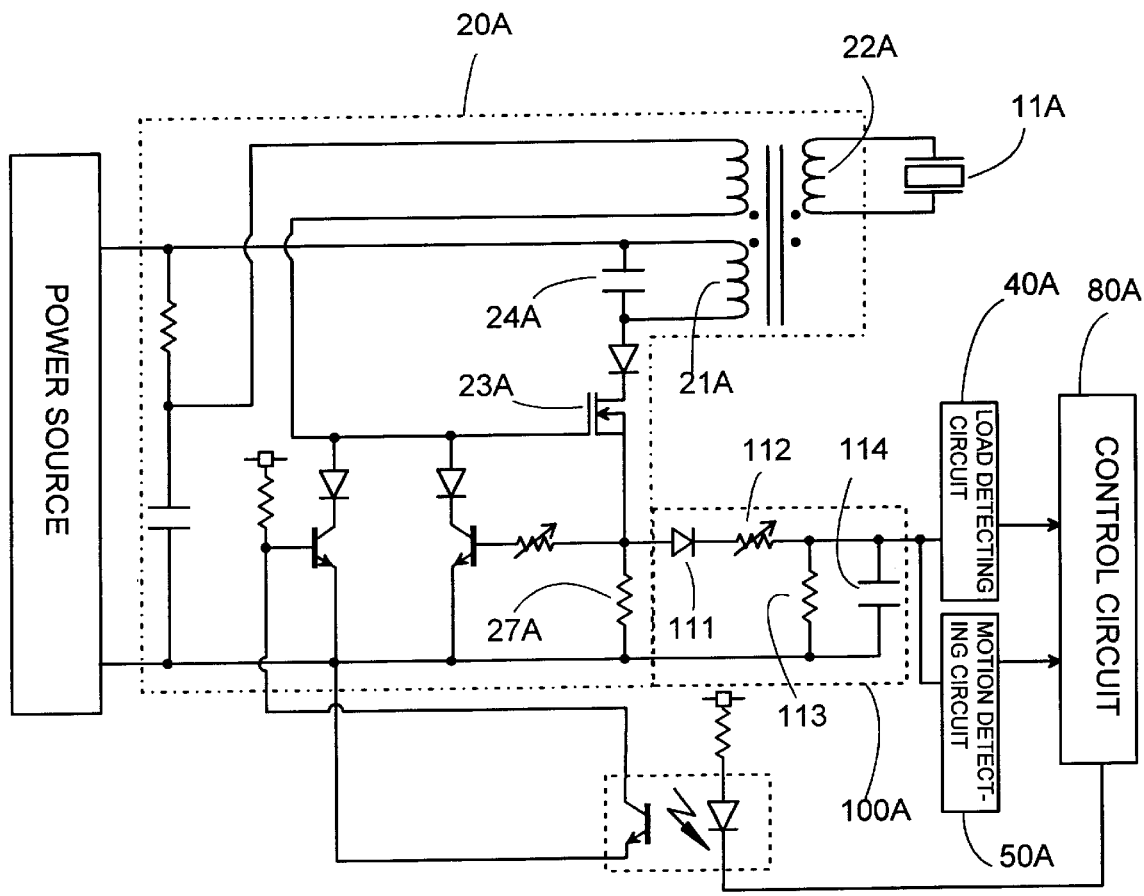
FIG. 8 is a circuit diagram of an ultrasonic wave applying apparatus in accordance with a second embodiment of the present invention.
Figure 9:
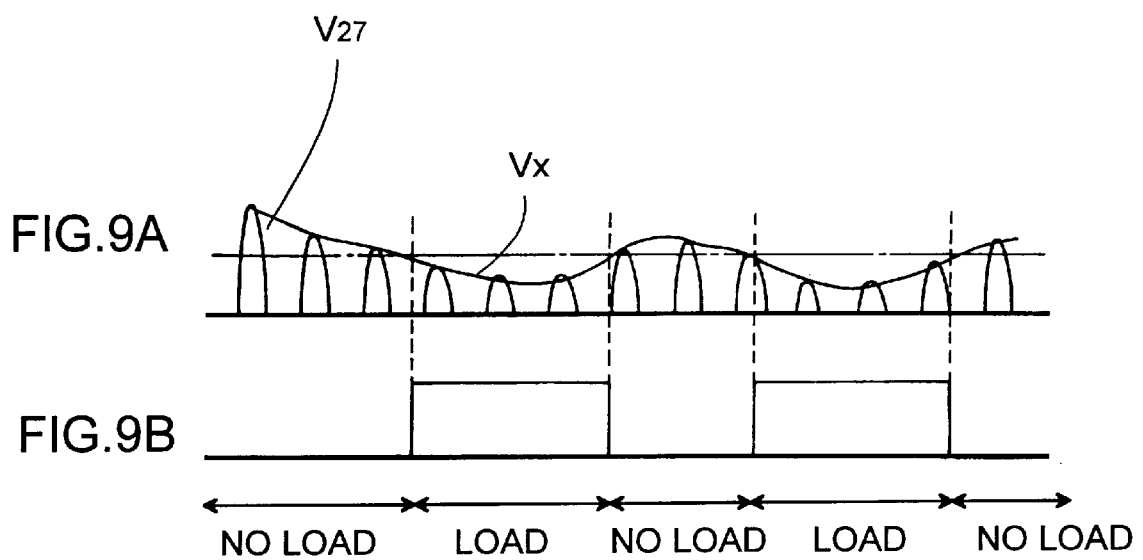
FIGS. 9A and 9B are explanatory views illustrating operations of the above apparatus.

FIG. 8 illustrates an oscillator circuit 20A and a monitoring circuit 100A of the ultrasonic wave applying apparatus in accordance with a second embodiment of the present invention. The other configurations are identical to those of the first embodiment. The oscillator circuit 20A has the basic configuration which is identical to that of the oscillator circuit 20 of the first embodiment, and therefore like parts are designated by like numerals with a suffix letter of "A". For example, secondary winding 22A is analogous to element 22 of FIG. 3 and vibration element 11A of FIG. 8 corresponds to element 11 of FIG. 3. The monitoring circuit 100A is configured to derive a monitoring output from a voltage appearing across a current sensing resistor 27A, which monitoring output is fed to a load detecting circuit 40A and a motion detecting circuit 50A. Upon occurrence of a load variation, a resonance voltage developed at the resonant circuit of a primary winding 21A and a capacitor 24A sees a corresponding voltage variation which appears across current sensing resistor 27A. Based upon this voltage variation, the monitoring circuit 100A provides the monitoring signal indicative of the load variation. The monitoring circuit 100A is composed of a series combination of a diode 111, a resistor 112, and a resistor 113 connected across the resistor 27A, and a capacitor 114 connected in parallel with resistor 111 so that, as shown in FIG. 9A, the voltage across resistor 27A is smoothed into a voltage across capacitor 114 of which voltage is fed as the monitoring signal Vx to load detecting circuit 40A and motion detecting circuit 50A. Load detecting circuit 40A issues load detection signal SL as shown in FIG. 9B when the level of monitoring signal Vx goes below a predetermined value. The motion detecting circuit 50A is of the same circuit configuration as that employed in the first embodiment of FIG. 3 and makes the motion detection based upon the monitoring output Vx.

Figure 10:
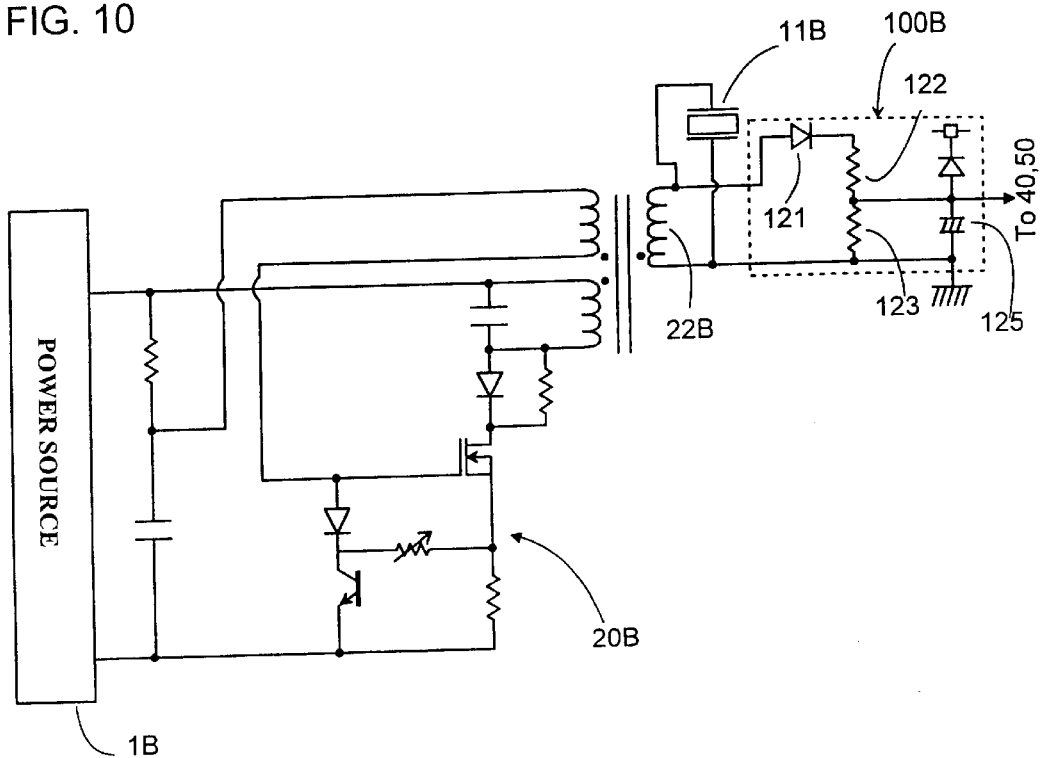
FIG. 10 is a circuit diagram of an ultrasonic wave applying apparatus in accordance with a third embodiment of the present invention.

FIG. 10 illustrates an oscillator circuit 20B and a monitoring circuit 100B of the ultrasonic wave applying apparatus in accordance with a third embodiment of the present invention. The other configurations are identical to those of the first embodiment. Thus, elements 1B, 11B, 40 and 50 correspond to a power source, a vibration element, a load detecting circuit, and a motion detecting circuit, respectively. The oscillator circuit 20B has the basic configuration which is identical to that of the oscillator circuit 20 of the first embodiment, and therefore like parts are designated by like numerals with a suffix letter of "B". The monitoring circuit 100B comprises a series combination of a diode 121, a resistor 122, and a resistor 123 connected across a secondary winding 22B of the oscillator circuit 20, and a capacitor 125 connected in parallel with resistor 123 so that the voltage developed at secondary winding 22B is rectified and smoothed into a voltage which is fed as the monitoring output to the load detecting circuit and the motion detecting circuit. The monitoring output thus obtained includes low frequency components representative of the load condition and the motion of the vibration plate ang gives a basis upon which the load and motion detection are made.

Figure 11:
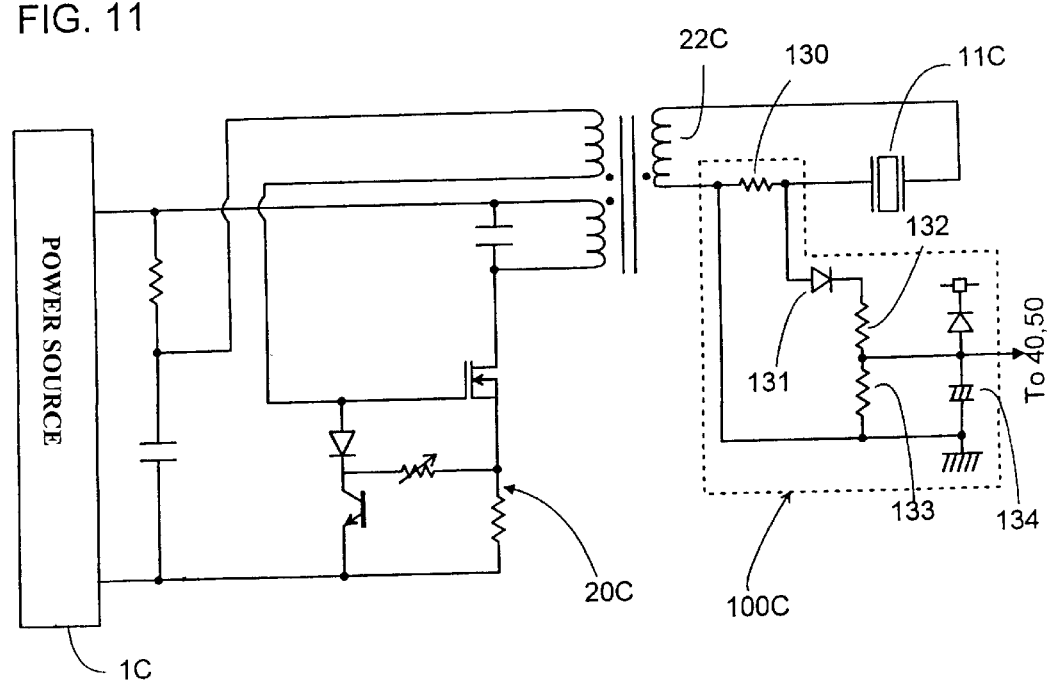
FIG. 11 is a circuit diagram of an ultrasonic wave applying apparatus in accordance with a fourth embodiment of the present invention.

FIG. 11 illustrates an oscillator circuit 20C and a monitoring circuit 100C of the ultrasonic wave applying apparatus in accordance with a fourth embodiment of the present invention. Thus, elements 1C, 40 and 50 correspond to a power source, a load detecting circuit, and a motion detecting circuit, respectively. The other configurations are identical to those of the first embodiment. The oscillator circuit 20C has the basic configuration which is identical to that of the oscillator circuit 20 of the first embodiment, and therefore like parts are designated by like numerals with a suffix letter of "C". The monitoring circuit 100C comprises a resistor 130 connected in series with the piezoelectric element 11C across the secondary winding 22C of the oscillator circuit 20C, a series combination of a diode 131, a resistor 132, and a resistor 133 connected across resistor 130, and a capacitor 134 connected across the resistor 133. Thus, the output voltage developed at the secondary winding 22C is rectified and smoothed to provide the resulting monitoring output to the load detecting circuit and the motion detecting circuit.

Figure 12:
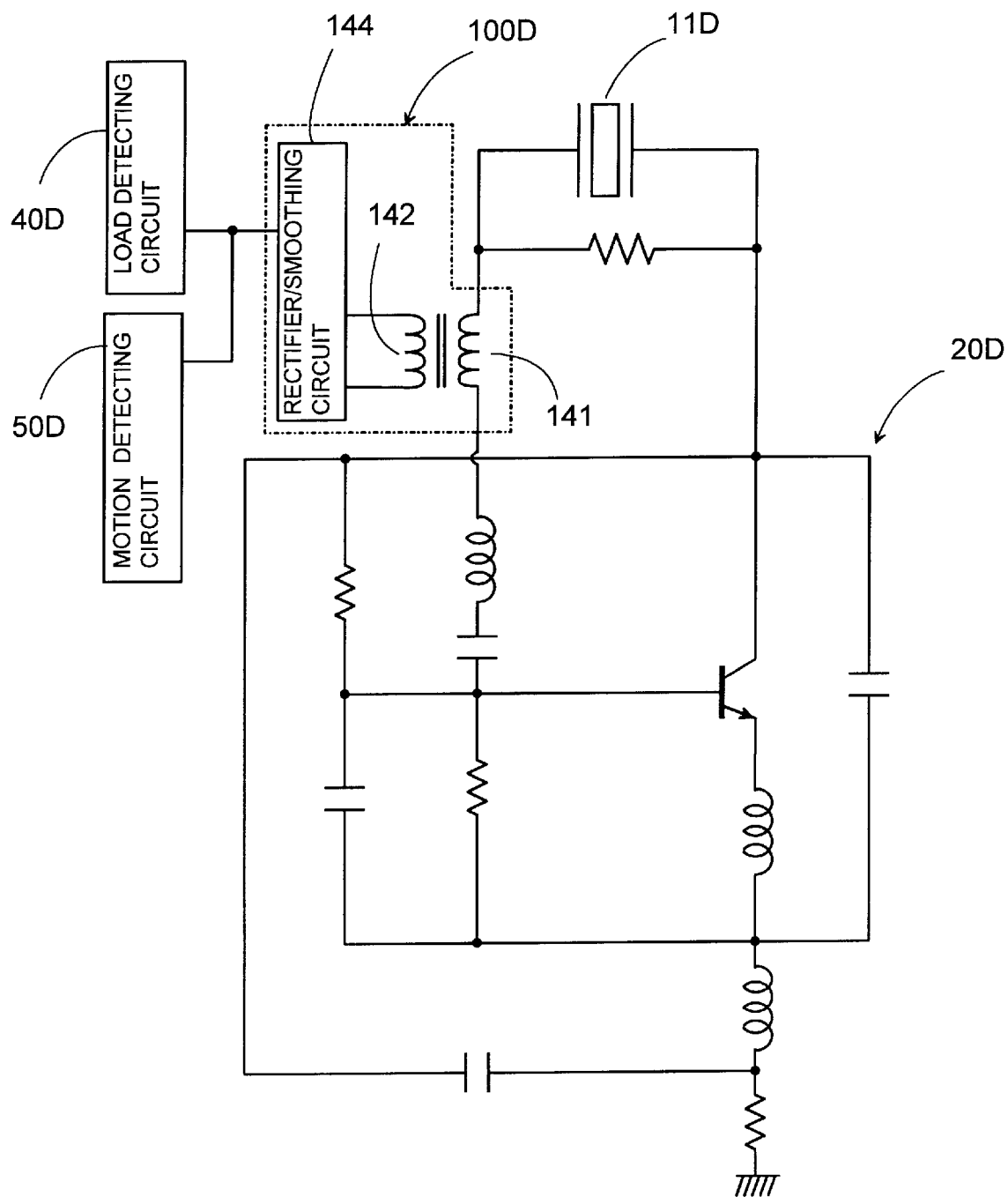
FIG. 12 is a circuit diagram of an ultrasonic wave applying apparatus in accordance with a fifth embodiment of the present invention.

FIG. 12 illustrates an oscillator circuit 20D and a monitoring circuit 100D of the ultrasonic wave applying apparatus in accordance with a fifth embodiment of the present invention. The other configurations are identical to those of the first embodiment. The oscillator circuit 20D is of Colpitts oscillator to have the piezoelectric element 11D connected in an output end of the circuit. The monitoring circuit 100D comprises a transformer with a primary winding 141 connected in series with the piezoelectric element 11D in the output path of the oscillator circuit 20D and with a secondary winding 142 magnetically coupled to the primary winding, and a rectifier/smoothing circuit 144 for rectifying and smoothing the output of the secondary winding. Thus, the monitoring output corresponding to voltage applied to the piezoelectric element 11D is fed to the load detecting circuit 40D and the motion detecting circuit 50D.

Figure 13:
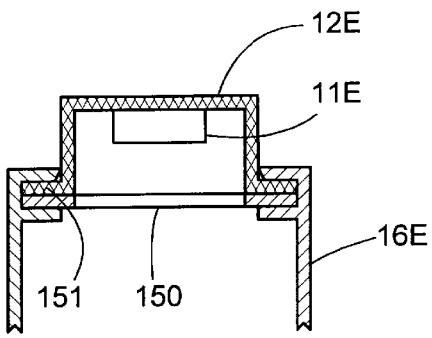
FIG. 13 is a sectional view of a sensor disk utilized for load detection and motion detection in an ultrasonic wave applying apparatus in accordance with a sixth embodiment of the present invention.
Figure 14A:
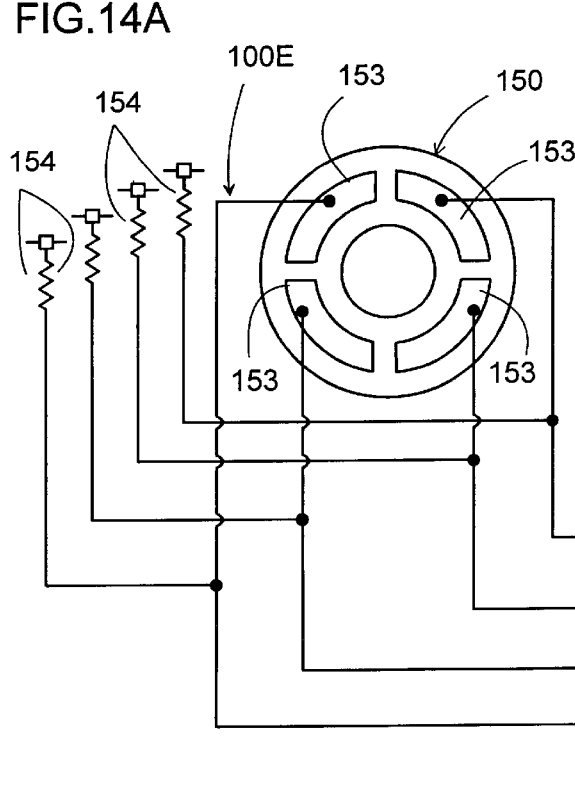
FIGS. 14A and 14B are planar views illustrating arrangement of electrodes on opposite surfaces of the sensor disk.
Figure 14B:
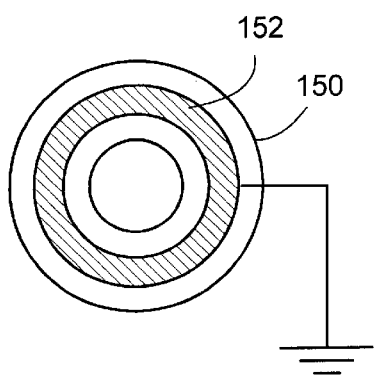
Figure 15:
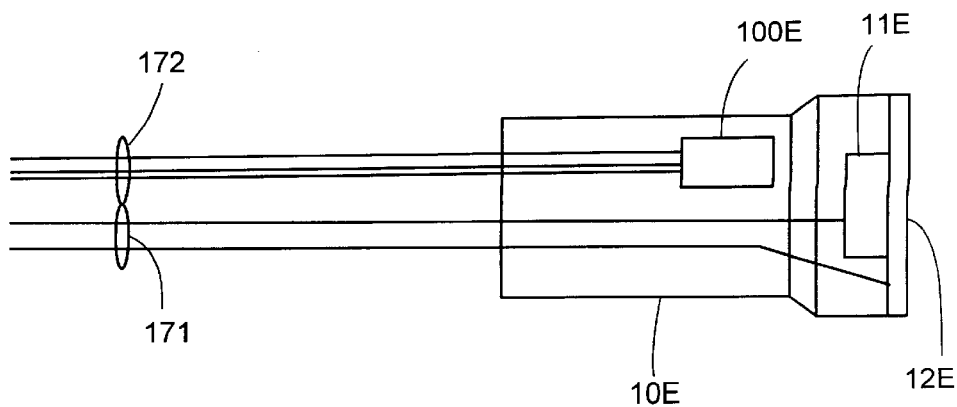
FIG. 15 is a schematic view illustrating wiring connection for transmitting an oscillating output to the applicator and the detected output therefrom in the above apparatus.

FIGS. 13, 14A and 14B illustrate a monitoring circuit 100E of the ultrasonic wave applying apparatus in accordance with a sixth embodiment of the present invention. Element 11E of FIG. 13 denotes a vibration element. The other configurations are identical to those of the first embodiment. The monitoring circuit 100E includes a ring-shaped sensor disk 150 made of pressure sensitive electro-conductive rubber which deforms in response to a force applied to the vibration plate. The sensor disk 150 is fitted in a recess at one end of a housing 16E of the applicator together with an end flange 151 of the vibration plate 12E and is capable of deforming as a consequence of the lo vibration plate 12E being subject to a force when the vibration plate 12E comes into contact with the human body and is caused to move across the skin of the human body in contact therewith. The sensor disk 150 varies its electrical resistance as being deformed, and is formed on its one surface with a single annular electrode 152, as shown in FIG. 14B and on the opposite surface with a plurality of circumferentially spaced electrodes 153, as shown in FIG. 14A. Each electrode 153 is connected to each of voltage sources 154 as well as to a load/motion detecting circuit 160 so as to provide the monitoring output in the form of a voltage in accordance with a deformation extent (resistance) of the sensor disk 150 at a portion corresponding to each of the electrodes 153. The load/motion detecting circuit 160 is composed of a microcomputer to make the load detection of determining whether the load is applied to the vibration plate based upon the monitoring signal from at least one of the electrodes 153 and to make the motion detection by analyzing the monitoring output from all of the electrodes 153. When the vibration plate 12E comes into contact with the human body, a resulting pressure causes the sensor disk 150 to vary its resistance, thereby giving a variation in the voltage between the electrode 152 and at least one of the electrodes 153. This voltage variation gives a basis on which the load detection is made. When the vibration plate 12E moves across the skin of the human body in contact therewith, the force applied to the vibration plate 12E will not uniformly exert on the sensor disk 150 so that different electrodes give different voltage. While, on the other hand, when the vibration plate 12E comes to a standstill, the four electrodes 153 give the same voltage. Thus, the vibration plate 12E is identified as moving upon detection of the voltage difference between the electrodes 153. As shown in FIG. 15, the monitoring circuit 100E accommodated in the applicator 10E transmits its output to the load/motion detecting circuit in the main housing through a wiring network 172 separated from a wiring network 171 transmitting an oscillation output to the piezoelectric element 11E. And, element 12E corresponds to a vibration plate.

Figure 16:
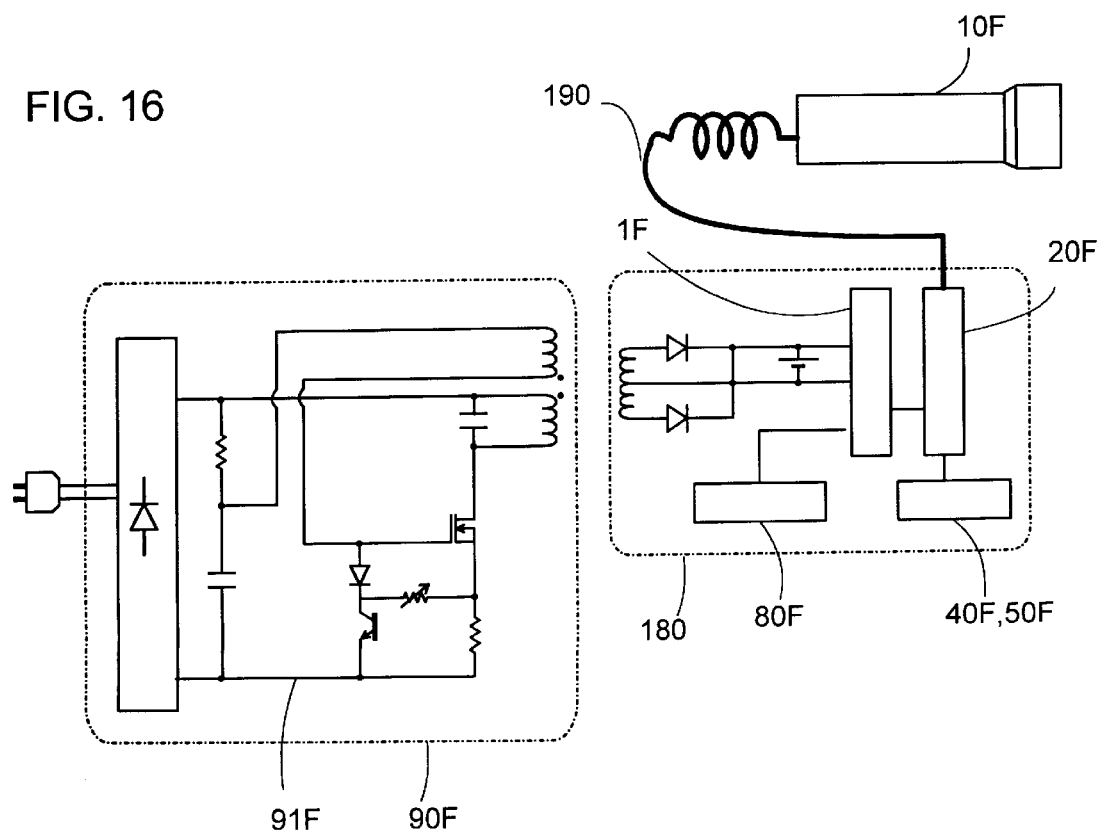
FIG. 16 is a circuit diagram of an ultrasonic wave applying apparatus in accordance with a seventh embodiment of the present invention.

FIG. 16 illustrates the ultrasonic wave applying device in accordance with a seventh embodiment of the present invention which has a basic configuration identical to that of the first embodiment of FIG. 2 and differs therefrom in that a sub unit 180 is provided in addition to the applicator 1OF and the main housing 90F. Element 91F denotes a changer circuit. The sub unit 180 accommodates the power source 1F, oscillator circuit 20F, load detecting circuit 40F, motion detecting circuit 50F, control circuit 80F all of the same configuration utilized in the first embodiment. The piezoelectric element and the vibrator plate are assembled in the applicator 10F. The applicator 10F has a water-tight housing and is connected to the sub unit 180 by way of a flexible cord 190 so that the vibration plate is driven by the oscillator circuit 20F to vibrate ultrasonically. With this arrangement, the applicator 10F can be made more compact, in addition to that the applicator 10F and the sub unit 180 can be easily designed to have water-tight structure suitable for use in a bathroom.

What is claimed is:

1. An ultrasonic wave applying apparatus comprising:
   a hand-held applicator device having a vibration element for contacting a skin of a user to apply ultrasonic waves to the skin;
   a power source providing a DC voltage;
   an oscillator circuit which is energized by the DC voltage from said power source to generate an oscillating output for driving said vibration element;
   a load detecting circuit which monitors whether said vibration element is loaded such as by contact with the skin and provides a load detection signal when said vibration element is so loaded;
   a motion detecting circuit which monitors whether said vibration element is moving and provides a motion detection signal when said vibration element is so moving;
   a control circuit which is connected to said load detecting circuit and said motion detecting circuit for controlling said oscillation circuit to lower said oscillating output being fed to said vibration element when said load detection signal is not received within a predetermined first time period or when said motion detection signal is not continuous over a critical time duration within a predetermined second time period even in the presence of said load detection signal being detected within said first time period.

2. The ultrasonic wave applying apparatus as set forth in claim 1, wherein a monitoring circuit is provided to give a single monitoring output indicative of the ultrasonic vibrations being effected by said vibration element and includes a low frequency component caused by moving said vibration element and having a frequency lower than that of said ultrasonic vibrations, said monitoring output being fed to said load detecting circuit and to said motion detecting circuit where it is processed to provide said load detection signal and said motion detection signal.

3. The ultrasonic wave applying apparatus as set forth in claim 2, wherein said oscillator circuit includes a transformer with a primary winding and a secondary winding across which said vibration element comprising a piezoelectric element is connected, said primary winding generating an oscillating voltage so that said secondary winding provides said oscillating output for driving said vibration element, said monitoring circuit comprising an auxiliary winding which is magnetically coupled to said transformer to provide said monitoring output.

4. The ultrasonic wave applying apparatus as set forth in claim 2, wherein said oscillator circuit includes a transformer with a primary winding and a secondary winding across which said vibration element comprising a piezoelectric element is connected, said primary winding generating an oscillating voltage so that said secondary winding provides said oscillating output for driving said vibration element,
   said monitoring circuit being connected across said secondary winding in parallel with said vibration element to rectify said oscillating voltage into said monitoring output in the form of a voltage.

5. The ultrasonic wave applying apparatus as set forth in claim 2, wherein said oscillator circuit comprises:
   a transformer with a primary winding and a secondary winding across which said vibration element comprising a piezoelectric element is connected;
   a capacitor being connected across said primary winding and cooperative with said primary winding to form a parallel resonant circuit; and
   a switching element connected in series with said parallel resonant circuit across a DC voltage source and driven to alternately turn on and off for causing said resonant circuit to provide an oscillating voltage which induces said oscillating output at said secondary winding;
   said monitoring circuit comprising a current sensing resistor connected in series with said switching element and said resonant circuit across said DC voltage to provide said monitoring output in the form of a voltage.

6. The ultrasonic wave applying apparatus as set forth in claim 2, wherein said monitoring circuit comprises a transformer with a primary winding and a secondary winding, said primary winding is connected in series with said vibration element comprising a piezoelectric element in an output path of said oscillator circuit so that said secondary winding provides said monitoring output.

7. The ultrasonic wave applying apparatus as set forth in claim 2, wherein said load detecting circuit comprises a comparator which compares an amplitude of said monitoring output with a predetermined level to provide said load detection signal when said amplitude deviates from said predetermined level by a certain extent.

8. The ultrasonic wave applying apparatus as set forth in claim 2, wherein said motion detecting circuit comprises a low-pass filter to derive said low frequency component from said monitoring output; and a judging circuit which provides said motion detection signal to said control circuit when an amplitude of said low frequency component exceeds a predetermined critical level.

9. The ultrasonic wave applying apparatus as set forth in claim 2, wherein said load detecting circuit comprises a comparator which compares an amplitude of said monitoring output with a predetermined level to provide said load detection signal when said amplitude deviates from said predetermined level by a certain extent, and wherein said motion detecting circuit comprises a low-pass filter to derive said low frequency component from said monitoring output; and a judging circuit which provides said motion detection signal to said control circuit when an amplitude of said low frequency component exceeds a predetermined critical level.

10. The ultrasonic wave applying apparatus as set forth in claim 1, further comprising:

a sensor disk disposed adjacent to said vibration element in a relation that said sensor disk is deformed as a consequence of said vibration element being loaded, said sensor disk comprising a pressure sensitive electroconductive rubber which varies electrical resistance when deformed, said sensor disk having on one surface a first electrode and on an opposite surface a plurality of second electrodes; and a plurality of voltage sources each applying a voltage between said first electrode and each of said second electrodes to provide a plurality of monitoring outputs representing a degree of deformation occurring at a portion of said sensor disk adjacent to each of said second electrodes;

said control circuit being configured to analyze at least one of said monitoring outputs to create said load detection signal and to compare all of said monitoring outputs with each other in order to create said motion detection signal.

11. The ultrasonic wave applying apparatus as set forth in claim 1, further comprising a temperature sensor which senses a temperature of said vibration element and provides a temperature output indicative thereof; and a protector circuit which, upon receiving said temperature output indicative of said temperature exceeding a critical level, produces a stop signal for disabling said oscillator circuit from generating said oscillating output.

12. The ultrasonic wave applying apparatus as set forth in claim 1, wherein said oscillator circuit produces said oscillating output intermittently in such a manner as to leave a rest period between adjacent pulse series of said oscillating output; said load detecting circuit and said motion detecting circuit being configured to transmit said load detection signal and said motion detection signal within said rest period to said control circuit.

13. The ultrasonic wave applying apparatus as set forth in claim 1, wherein said oscillator circuit and said power source are incorporated within said hand-held applicator together with a battery which supplies a source voltage to said power source, said hand-held applicator being physically detachable from a main housing which incorporates an inverter providing an AC voltage, said inverter including a primary power winding across which said AC voltage is developed, said hand-held applicator incorporating therein a secondary power winding which is magnetically coupled to said primary power winding to induce a corresponding voltage when said applicator is physically connected to said main housing, said secondary power winding being connected within said hand-held applicator to charge said battery by said voltage induced on said secondary power winding.

14. An ultrasonic wave applying apparatus comprising:

a hand-held applicator device having a vibration element for contacting a skin of a user;

a power source;

an oscillator circuit energized by said power source that generates an oscillating output for driving said vibration element;

a skin contacting detecting circuit for monitoring whether said vibrating element is in contact with a skin of a user;

a motion detecting circuit for monitoring whether said vibrating element is moving and providing a detection signal when movement of the vibration element occurs;

a control circuit connected to said skin contacting detecting circuit and said motion detecting circuit to lower said oscillating output when a signal from said skin contacting detecting circuit is not received within a first time period or when said motion detection signal is discontinuous over a critical time duration within a second time period.

* * * * *